(12) United States Patent
Gransæther

(10) Patent No.: US 9,151,700 B2
(45) Date of Patent: Oct. 6, 2015

(54) FLUID SAMPLING ASSEMBLY

(75) Inventor: Eivind S. Gransæther, Stavanger (NO)

(73) Assignee: Mirmorax AS, Stavanger (NO)

( * ) Notice: Subject to any disclaimer, the term of this patent is extended or adjusted under 35 U.S.C. 154(b) by 442 days.

(21) Appl. No.: 13/522,553

(22) PCT Filed: Feb. 4, 2011

(86) PCT No.: PCT/NO2011/000046
§ 371 (c)(1),
(2), (4) Date: Jul. 17, 2012

(87) PCT Pub. No.: WO2011/096823
PCT Pub. Date: Aug. 11, 2011

(65) Prior Publication Data
US 2012/0291568 A1 Nov. 22, 2012

(30) Foreign Application Priority Data
Feb. 4, 2010 (NO) .................................. 20100183

(51) Int. Cl.
*G01N 1/20* (2006.01)
(52) U.S. Cl.
CPC ...... *G01N 1/2035* (2013.01); *G01N 2001/2057* (2013.01)
(58) Field of Classification Search
CPC ........ E21B 49/08; G01N 1/2035; G01N 1/02; G01N 30/20; F16K 47/045; F16K 1/14
See application file for complete search history.

(56) References Cited

U.S. PATENT DOCUMENTS

| 3,345,032 | A | * | 10/1967 | Rawstron | 251/172 |
| 3,985,150 | A | * | 10/1976 | Kindersley | 137/240 |
| 4,628,732 | A | * | 12/1986 | Makinen | 73/866.5 |
| 5,452,620 | A | * | 9/1995 | Giannone | 73/864.31 |
| 6,205,869 | B1 | * | 3/2001 | Schadt et al. | 73/863.71 |
| 6,792,818 | B2 | * | 9/2004 | Jaeger | 73/863.86 |
| 6,860,162 | B1 | * | 3/2005 | Jaeger | 73/863.85 |
| 7,025,330 | B2 | * | 4/2006 | Massey | 251/315.1 |
| 7,481,124 | B2 | * | 1/2009 | Schadt | 73/863.86 |
| 2002/0134442 | A1 | * | 9/2002 | Wang | 137/625.46 |
| 2003/0188588 | A1 | * | 10/2003 | Jaeger | 73/863.84 |
| 2007/0272038 | A1 | * | 11/2007 | Schadt | 73/864.01 |

FOREIGN PATENT DOCUMENTS

| GB | 1269166 A | * | 4/1972 |
| NL | 9001848 A1 | * | 3/1992 |
| NL | 1003224 C2 | * | 12/1997 |
| WO | WO 0051923 A1 | * | 9/2000 |
| WO | WO-02/086455 A1 | | 10/2002 |
| WO | WO-2008/056097 A2 | | 5/2008 |

OTHER PUBLICATIONS

Kalland, Bjorn Inge, "International Search Report" for PCT/NO2011/000046 as mailed May 2, 2011, 3 pages.

* cited by examiner

*Primary Examiner* — David A Rogers
(74) *Attorney, Agent, or Firm* — Winstead PC

(57) ABSTRACT

Sampling arrangement adapted for extracting a fluid sample from a fluid flowing in a flow path. The arrangement comprises a sampling valve, such as a ball valve, comprising an outer body and an inner body rotationally supported within it. The inner body is rotationally supported about a rotation axis and comprises a cavity with a first opening adapted to be rotated into and out of fluid connection with the flowing fluid, and a second opening which faces in a direction parallel to the rotation axis of the inner rotating body.

14 Claims, 9 Drawing Sheets

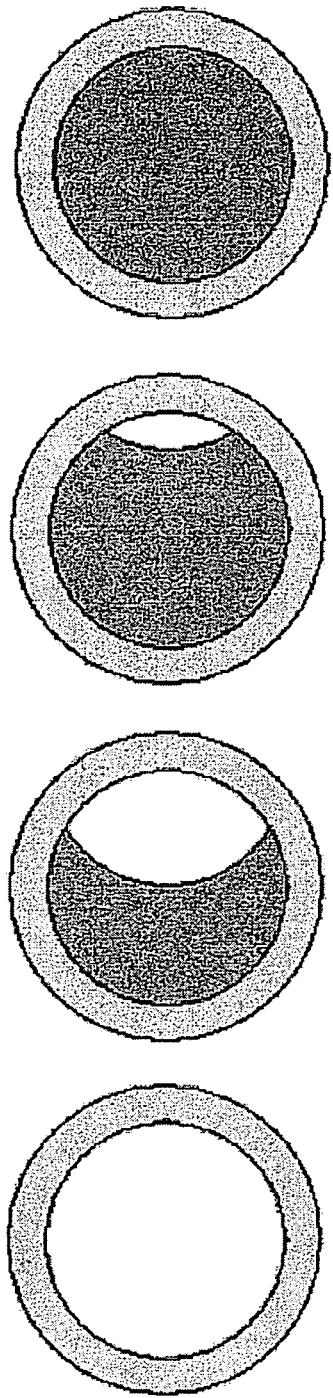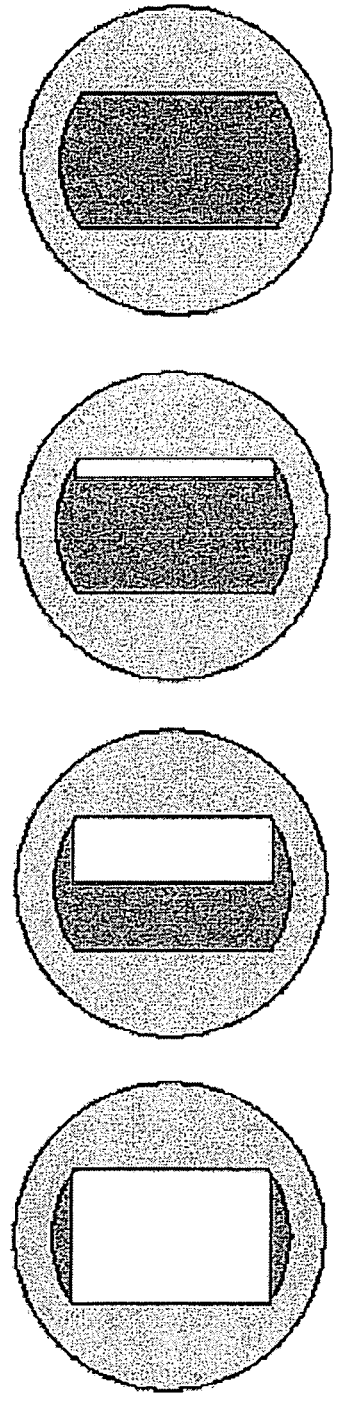

From the outside

FLUID SAMPLING ASSEMBLY

The present invention relates to assemblies adapted to provide a representative sample from a flow of fluid containing hydrocarbon. More particularly, the invention relates to such assemblies which can be employed without halting the flow and under the existing pressure in the flow.

BACKGROUND

For systems that are used for production of oil and gas it is of interest to know the cut of oil, gas, water and other components in the mixture that arise from each separate oil well (the process fluid). This knowledge is of value for those who seek to optimize the production, as knowledge about the production in each separate well will form basis for how the oil is to be produced, with the object of obtaining as most oil and gas as possible. It also has value in situations where different owners of the oil wells want to know how much of the total incomes they can claim.

In order to do this there exist today a variety of metering equipment which provide measured data on central parameters, but which are not considered sufficiently stable for giving equally good data over time. The value of the data is precisely associated with the gain from the use, namely increased recovery from the reservoir, and is hence high for the owner. In order to calibrate these meters, one must use a known liquid to calibrate against or precisely know the components of what is being measured. To employ a known liquid is associated with shutting down the oil production during the time of calibration, and is associated with uncertainty with regards to two aspects; on one hand one will never know if the known liquid is polluted and thus whether the calibration is correct. On the other hand there is uncertainty associated with whether shutting down production will lead to a permanent or temporarily reduced production. Shutting down the production is very expensive, the quality of the calibration is uncertain, and due to these reasons the method is in practice not used.

In addition, the existing metering technology does not take account for future need of data, since the measuring principles and the installed technology is closely connected with the data that are needed today. There is a plurality of characteristics of the process fluid which is of interest today, which is not possible to measure with current technology, being either natural components or artificially added components.

To solve the problem of calibration and collecting knowledge of unknown components, one may use a technique where one extracts a representative sample of the process fluid and analyzes this sample in a laboratory, so that the components become known.

In order to do this, one uses today a traditional bleed point, where it is arranged a connection point to the pipe from which one wants to extract a sample, and then the differential pressure is used to bleed off a sample of the process fluid. The sample may either be guided through pipe (test lines) to the manned operation central on land or up to the platform offshore, or be used to fill a container which is transported to the same central for analysis. There is a plurality of problems associated with this technique, both with regards to cost and degree of representativity. Due to the bleed point being arranged at a particular place, the sample will be very dependent of the process fluid being representative. This is, however, very difficult to foresee, since the flow regime and mixture vary among applications and along the lifetime of the well. In addition, the bleed point is not designed for collecting a sample of dynamic flow and one therefore has not a good overview of whether the amount of for instance liquid and particles is representative for the distribution in the process fluid.

By using test lines and external pressure tank for sample extraction, the outlet and pipe system may be exposed to pollution from settling and blocking, which again leads to poor representation of the process fluid.

In addition there exists a technique that uses an installed branching of the bleed gate, shaped like an octopus having three-four smaller pipes. The smaller pipes are arranged at various positions in the cross section and end in a pipe that leads to the bleed gate and has the purpose of increasing the chance for the process fluid to be representative by pulling samples simultaneously from various places in the cross section of the pipe. These installations are permanent and are exposed to the same problematic issues as described with regard to pollution, blocking and that non-equal differential pressure in the various pipes result in unlike representation.

The geometric shape of the system is also not suited for installation without halting the production of oil and it is thus not of interest to install this technology each time one is about to extract a sample. That means that the state of the art, as described above, with its limitations, is not suited for use in another way in order to improve the result.

International patent application WO02/086455 describes a method and an arrangement for taking samples from a multiphase fluid mixture. The fluid sample is collected in a phase separator by means of valve actuation, where the phases can be divided and a sample that contains the water phase can be transferred to a sample bottle for analysis.

Furthermore, the international patent application WO2008/056097 describes a system and method for providing a fluid or gas sample from a multiphase mixture that flows in a hydrocarbon conducting pipe.

The invention described in the following solves the described problems, significantly reduces the sources for possible errors and thus leads to a very high degree of representativity for the process fluid sample.

The Invention

According to a first aspect of the invention there is provided a sampling arrangement adapted for extracting fluid sample from a fluid flowing in a flow path. The sampling arrangement comprises a sampling valve, such as a ball valve, comprising an outer body with an inner rotating body supported within this. The inner body is suspended in a rotating manner about a rotational axis and comprises a cavity with a first opening adapted to be rotated into and out of fluid communication with the flowing fluid. The inner body also comprises a second opening which faces in a direction parallel with the rotational axis of the inner rotating body.

The term parallel is used in its widest sense, as it is meant to comprise the meaning of at least partially parallel. There may thus exist an angle between the parallel and the direction in which the second opening faces. However, it is preferred that the second opening faces in a strictly parallel direction, with regard to the rotational axis.

In an embodiment of the first aspect of the present invention there may thus be a ball valve, wherein the ball has an inner cavity with two openings. One opening can, in a closable manner, open for entrance of the fluid into the inner cavity. The second opening can either be used for outflow of the fluid (the fluid sample), or may be used for insertion of a sampling organ for collecting/capturing the fluid in the inner cavity.

With such a sampling arrangement it is rendered possible that the fluid can flow in a horizontal direction into the inner cavity, so that good representativity for the fluid in the inner cavity is provided. In addition, the fluid sample can be led out in a vertical direction, either by flowing out as a result of a pressure difference, or by taking out a sample by means of an arrangement adapted for this purpose.

According to a second aspect of the present invention there is suggested an assembly which is adapted to provide a sample from a flowing fluid that flows in a flow path. The assembly comprises a releasable part and a fixed part which is adapted for releasable connection to the releasable part. The fixed part comprises a receiving chamber which is provided with a closable fluid opening for fluid communication with the flowing fluid and a closable receiving opening for reception of a sampling organ into the receiving chamber. The releasable part comprises said sampling organ, which is adapted to be moved into the receiving chamber when the releasable part is connected to the fixed part.

The sampling organ preferably comprises a closable cavity for confining a sample of the flowing fluid.

The assembly according to the second aspect of the invention can be adapted in such way that the receiving chamber is arranged in the ball of a ball valve, wherein the ball has a cavity with an opening that makes the said closable fluid opening, as well as an opening for receiving the sampling organ. It will be appreciated that in lieu of a ball, there may be a cylinder or other type of shape with an inner cavity, which can be rotated within the valve.

In one embodiment the ball can be rotated about a rotational axis and the rotational axis is parallel with the opening for receiving the sampling organ and/or extends through this opening. As stated above, the term parallel is not limited to strictly parallel, but indicates the consequence of comprising a parallel component.

The fixed part can be connected to the flow path in connection with a flow obstacle which provides mixing of the components of the flowing fluid in the area of the receiving chamber.

The flow obstacle can be a change of direction of the flow direction. The fixed part can be attached to a blind end of a T-shaped part of the flow path.

The flow obstacle can also be in the form of a constriction of the flow cross section. This can, for instance, be provided for in the form of a simple constriction, a venturi shape or a ball.

According to an embodiment of the second aspect of the invention, the sampling organ is bar-shaped and has a section with constricted cross section that constitutes the closable cavity. Moreover, the releasable part can comprise a sample sleeve which is arranged to slide over the sampling organ, and is adapted to be slid over the section with constricted cross section. The sample sleeve can thus seal against a head in the one end of the section with constricted cross section.

In an alternative embodiment of the second aspect of the present invention the sampling organ is provided with a plurality of mouths and connected sample channels which are adapted to pull in a volume of the flowing fluid in the receiving chamber. At least some of the mouths are arranged at different axial position on the sampling organs. In this way it is ensured that fluid is taken from different vertical levels. With such an embodiment the sampling organ can further comprise a common sample channel for guiding away a fluid sample which has been pulled in through the mouths. In this manner the sampling organ can be put in condition to pull in a new fluid sample from the receiving chamber. Such a solution makes instantaneous repetition of the sampling possible. That is, the sampling organ does not have to be led in and out for each sampling. On the contrary, a first sample can be taken through the mouths, then the receiving chamber can again be filled with fluid from the flowing fluid for a second sampling, and so on. One can also imagine that fluid samples are taken at regular intervals without the fluid communication between the receiving chamber and the flowing fluid being closed between each time.

In one embodiment the closable receiving opening for receiving a sampling organ can comprise a ball valve with a through bore. When the releasable part is not attached to the fixed part, the closeable receiving opening will function as one barrier (preferably one of more barriers) between the flowing fluid and the surroundings.

According to a third aspect of the present invention there is provided an assembly for characterizing a fluid, comprising an insertion organ which is adapted to be inserted into a cavity with the fluid which is to be characterized. The assembly comprises an axially movable organ with a constricted part and a head;
an outer sleeve adapted to be moved in axial direction over the constricted part and the head, so that a confined cavity is formed between the constricted part;
wherein
the axially movable organ is adapted to be moved so that the axial extension of the confined cavity is reduced.

This assembly, according to the third aspect of the invention, is advantageously suitable for converting the gas phase into liquid phase by means of pressure. The axially movable organ preferably comprises a hydraulic actuation piston.

The assembly according to the third aspect of the invention is suited to measure the volume amount of the gas phase in a fluid sample in situ. This is done by measuring how much the volume is reduced when the gas phase is compressed in the said confined cavity.

According to a fourth aspect of the invention there is provided a sampling organ for collecting a fluid sample, adapted to be inserted into a cavity comprising a fluid. The sampling organ is provided with a plurality of mouths and connected sample channels which are adapted to pull in a volume of the flow fluid in the receiving chamber. At least some of the mouths are arranged in different axial position on the sampling organ.

The sampling organ advantageously comprises a common sample channel for guiding away a fluid sample pulled in through the mouths. In this manner the sampling organ can be put in condition to pull in a new fluid sample from the receiving chamber.

One embodiment of the fourth aspect of the present invention is characterized in
that in the common sample channel there is arranged a one-way valve for flowing in the direction away from the sample channels and that the common sample channel is in fluid communication with the sample channels through respective collecting channels;
that the sample channels and the collecting channels are provided with one-way valves adapted for flow from the mouths in direction towards the common sample channel;
that to each sample channel there is allocated a sample piston adapted to provide negative pressure for pulling in fluid sample and positive pressure for conducting the fluid sample into the common sample channel.

According to a fifth aspect of the present invention there is provided a sampling organ for collection of a fluid sample, adapted to be inserted into a cavity comprising a fluid. The sampling organ comprises a bar-shaped body with a section having constricted cross section, wherein a head is in the end of the constricted cross section, and further comprising an, arranged on the bar-shaped body and axially slideable, outer sleeve that is adapted to be moved over the constricted cross section and to seal against the head, so that it encloses a confined cavity between its inner face and the constricted cross section.

A common advantage of the various aspects of the present invention is that they make it possible to take one or more fluid samples from a flowing fluid without requiring a halt of the flow for the sample extraction.

EXAMPLE DESCRIPTION

While a general description of the invention is given above, a non-limiting description of an embodiment of the invention will be given in the following. The embodiment is described with reference to the figures, wherein FIG. 1 shows a schematic cross section view of the assembly according to the invention;

FIG. 9 shows the opening cross section of a ball valve in various positions;

FIG. 10 shows the opening cross section of another ball valve in various positions;

Figure 1:
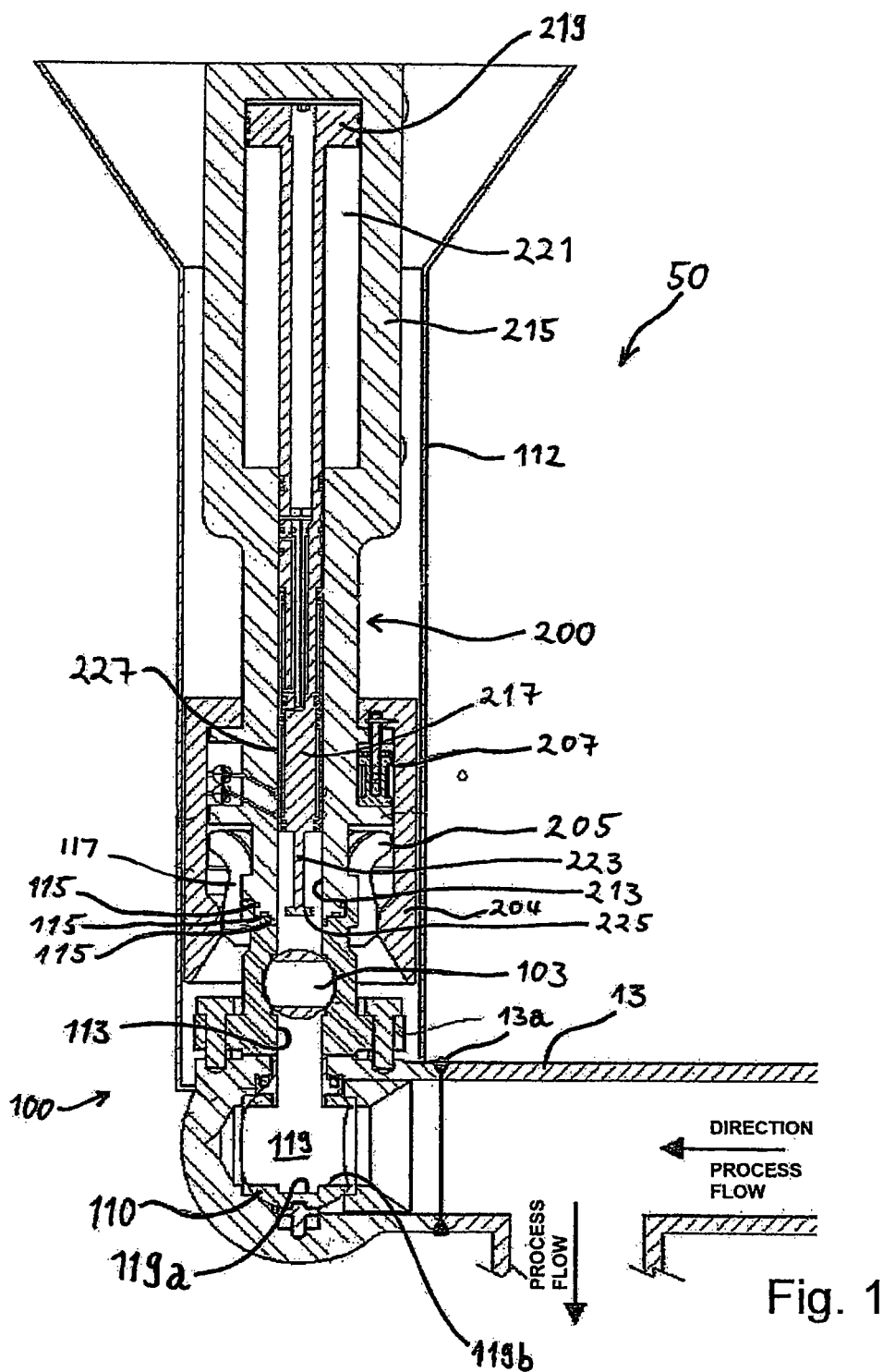

It is first referred to FIG. 1, as a description of an example embodiment according to the first aspect of the invention will be given. Here it is shown a flow path 13 in which a fluid flows. Onto the flow path 13 there is welded a sampling valve in the form of a ball valve 110. The ball valve 110 comprises an inner rotating body in the form of a ball which is provided with a cavity 119. The ball or its cavity is provided with a first opening 119*b* which can open and close for fluid communication with the flowing fluid by means of rotation of the ball about a vertical rotational axis. In FIG. 1 the first opening 119*b* is shown in an open position. By rotating the ball about the rotational axis the first opening 119*b* can be closed so that a sample of the flowing fluid can be confined within the cavity 119. There is also arranged a second opening 113 which faces in a vertical direction. In this embodiment the second opening faces parallel and coaxially with the rotational axis. The second opening can be closed with a barrier valve 103.

Through the second opening 113 the fluid sample can be let out of the cavity 119 by means of pressure difference, for instance to a container which is connected directly to the ball valve or on, in FIG. 1, the upper side of the barrier valve 103. Alternatively, a sampling organ can be inserted into the cavity 119 of the ball valve 110 and confine the sample inside the cavity 119 itself, or in another way guide the fluid out from the cavity 119.

One can also imagine a solution where the cavity 119 of the ball valve 110 (or other type of valve with a rotating body with cavity) has only one closable opening 119*b*. The fluid sample would then immediately be let out from the cavity 119 in a horizontal direction, if the rotational axis is vertical, as shown in FIG. 1.

In the following, it is again referred to FIG. 1, for a description of an example of an embodiment of the second aspect of the present invention. FIG. 1 shows an assembly 50 according to the invention, for sample extraction from a fluid flow. The assembly is arranged with a closable fluid connection to a flow path 13 for a process fluid. In this example embodiment the flow path is a pipe assembly 13 on the seabed that guides a flow of hydrocarbon-containing fluid in connection with one or more subsea wells. The fluid mainly comprises hydrocarbons in liquid phase and in gas phase, as well as water. The assembly 50 is attached to the pipe assembly 13 by means of welding, as shown in FIG. 1 with the weld 13*a*. The arrows indicate the flow direction. Moreover, the assembly 50 according to the invention is attached to the pipe assembly 13 in the blind end of a T-piece. Due to the T-piece, the fluid flow in the pipe assembly 13 makes a substantial change of direction. In the blind part of the T-piece, it is thereby achieved a good mixture of the composition of the flowing fluid, both with regards to various phases as well as components.

The assembly 50 according to the invention comprises a fixed part 100 and a releasable part 200. The fixed part 100 is welded to the pipe assembly 13, as described above. Furthermore, the fixed part 100 is adapted to receive the releasable part 200, as the releasable part can be connected to the fixed part by means of an ROV (remotely operated vehicle).

The releasable connection between the releasable part 200 and the fixed part is provided by a locking mechanism comprising dogs 205 and an actuation sleeve 204. The actuation sleeve 204 is hydraulically actuated by means of a plurality of hydraulic pistons 207, and leads the dogs 205 into engagement with a locking profile 117 in the fixed part 100. The dogs 205 can be led out of engagement by moving the actuation sleeve 204 the opposite direction. A plurality of seals 115 provides a fluid tight connection between the fixed part and the releasable part.

In the following a course of events for sampling is described, where the releasable part 200 is connected to the fixed part 100, after which a sample is taken, and wherein at the end the releasable part 200, inclusive the fluid sample, is again released from the fixed part 100.

Again it is referred to FIG. 1. Before the releasable part 200 is connected to the fixed part 100, as described above, a chamber valve 110 is turned 90 degrees about the vertical axis so as to seal against the fluid flow in the pipe assembly 13. A barrier valve 103 is also closed. In the shown example of embodiment the barrier valve 103 is also in the form of a ball valve. The chamber valve 110 is in the shown example in form of a ball valve with a receiving chamber 119 in the ball.

The fixed part 100 comprises an outer sleeve 112 with a funnel-shaped end, for reception of the releasable part 200. When the releasable part 200 is connected to the fixed part 100 by actuation of the dogs 205, by means of an ROV (not shown), there is performed pressure test of the seals 115 and the barrier valve 103.

Since those of the seals 115 that face radially outwards begin to seal already as the releasable part 200 starts to get into engagement with the fixed part 100, the piston 219 will move a bit backwards, that is further into the main body 215. This is to avoid hydrostatic problems during connection between the releasable part 200 and the fixed part 100.

Figure 2:
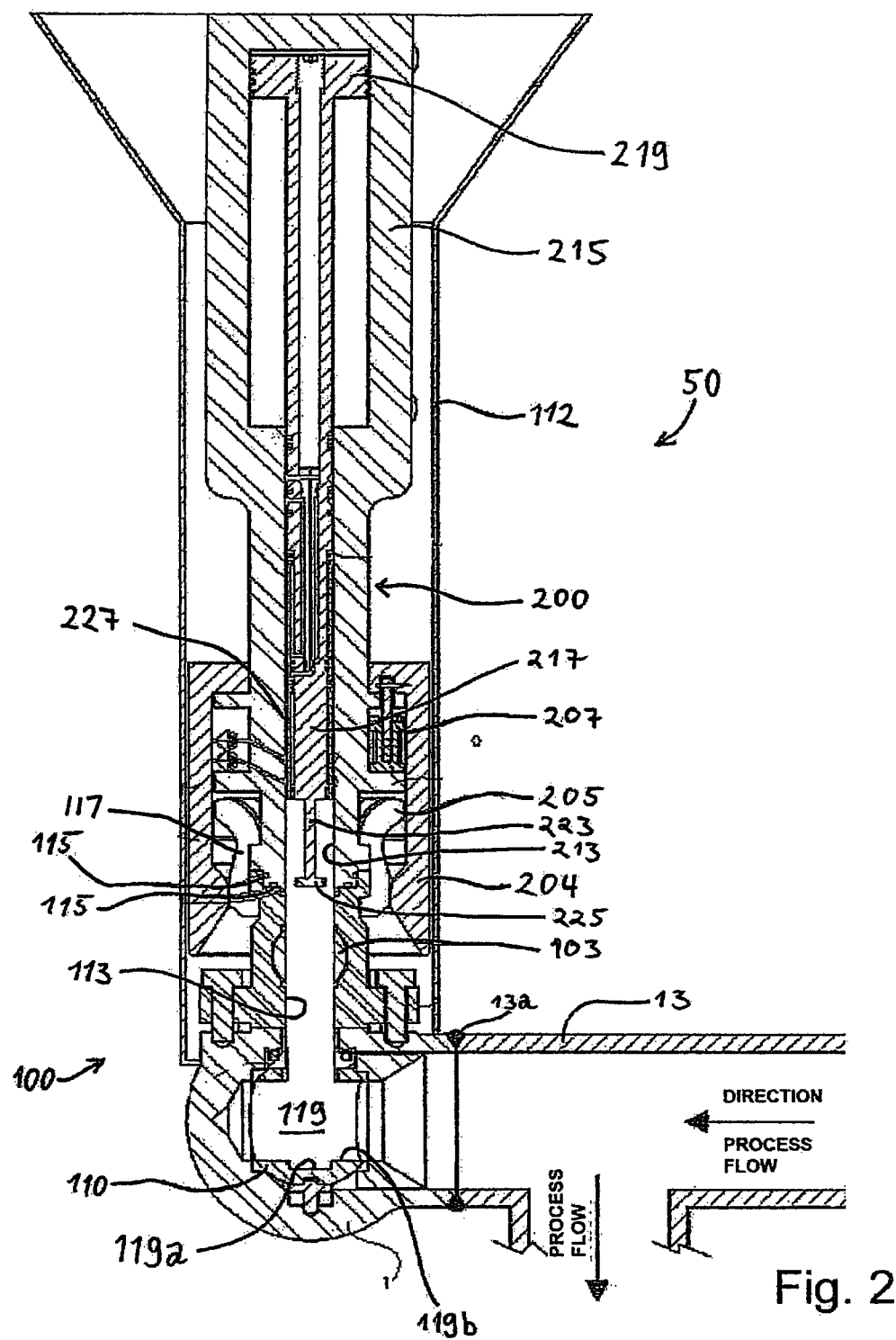
FIG. 2 shows a schematic cross section view of the assembly in FIG. 1, where a barrier valve is opened.

Thereafter the barrier valve 103 can be opened, as illustrated in FIG. 2. After the barrier valve 103 has been opened there is preferably performed another pressure test. Then the chamber valve 110 is opened, so that a fluid connection exists between a bore 213 in the releasable part 200 and the fluid flow in the pipe assembly 13. The bore 213 is arranged in a main body 215 of the releasable part 200 and the barrier valve 103 is arranged in connection with a bore 113 in the fixed part 100. The bore 213 in the releasable part 200 is in line with the bore 113 of the fixed part 100.

Turning of the valves can be performed in any appropriate manner and is considered known to the person skilled in the art. They can for instance be turned by means of hydraulics or mechanically.

Figure 3:
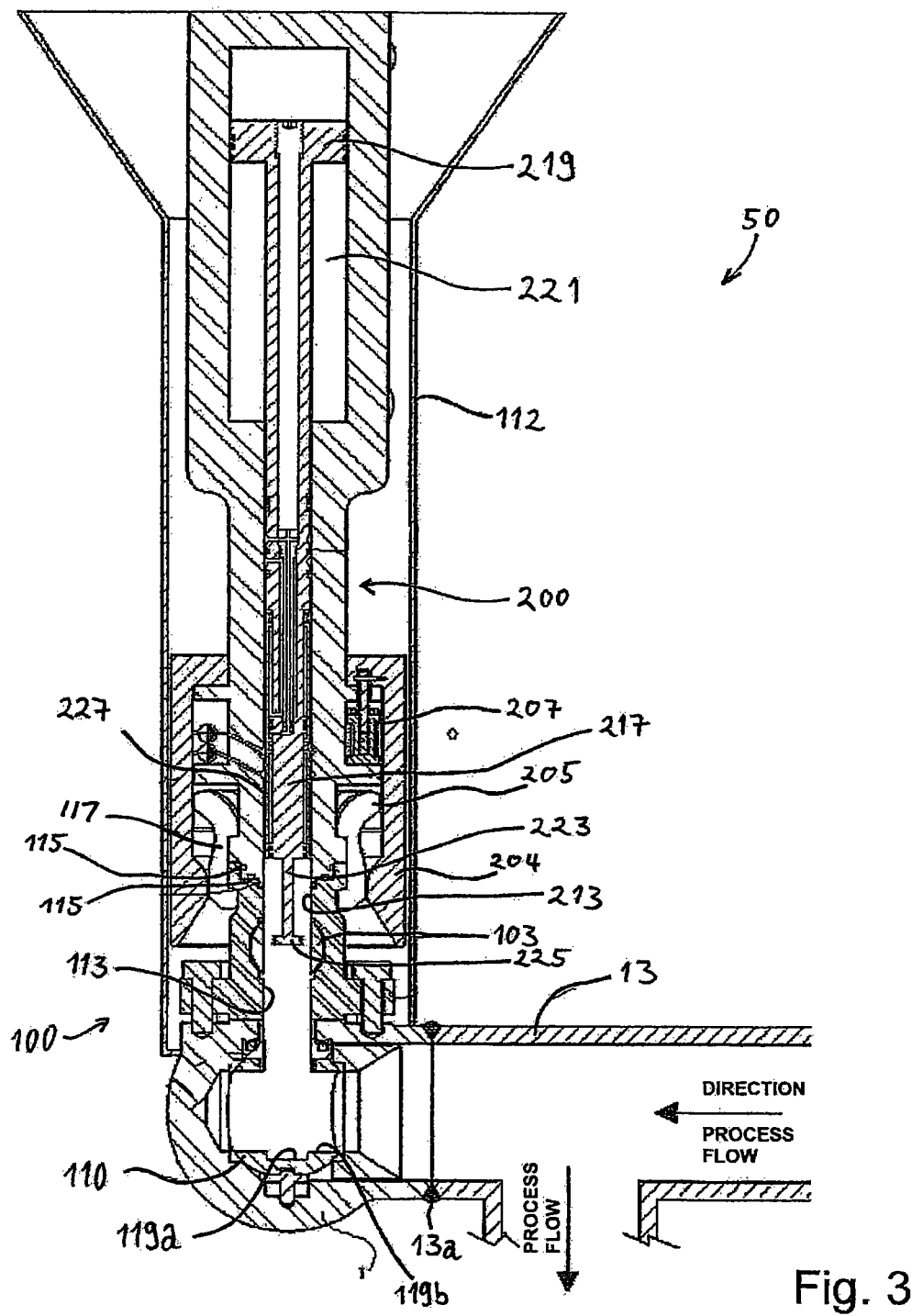
FIG. 3 shows a schematic cross section view of the assembly in FIG. 1, where a sampling organ is moved towards a receiving chamber.
Figure 4:
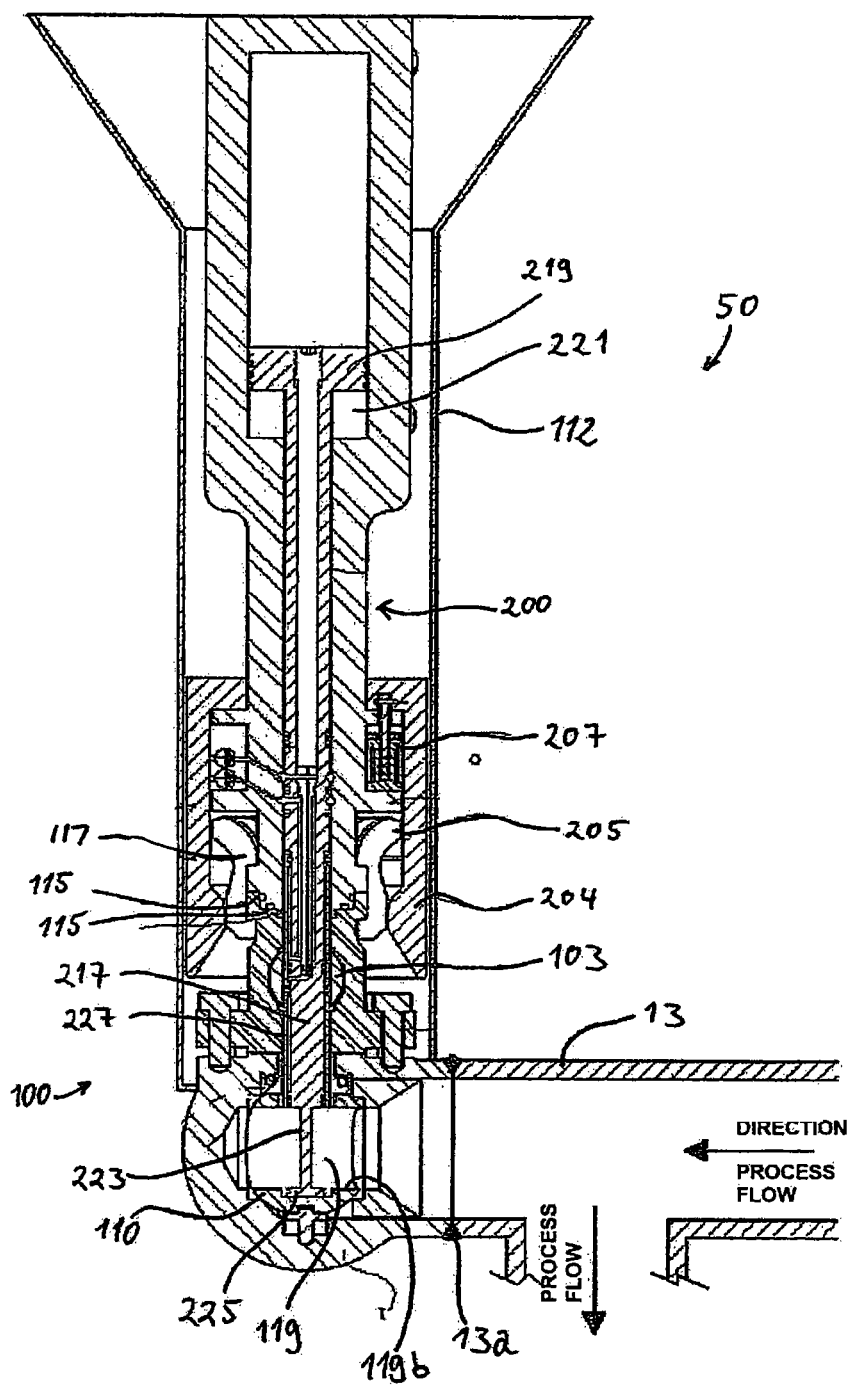
FIG. 4 shows a schematic cross section view of the assembly in FIG. 1, where a sampling arrangement is inserted into the receiving chamber.

Thereafter a sampling organ 217 is led through the opening in the barrier valve 103, as shown in FIG. 3. The sampling organ 217 is suspended in the bore 213 and comprises a piston 219 in one of its ends. The piston 219 is arranged in a piston chamber 221 in the main body, so that the sampling organ can be led forwards and backwards through the bore 213 by means of hydraulic pressure. As will be understood by a person skilled in the art the sampling organ 217 can also be actuated in another way, for instance with an electrical actuator.

In its opposite end the sampling organ 217 has a sample volume which is defined by a constricted diameter 223 a distance along the sampling organ 217. At the end of this distance there is a head 225 with peripherally arranged seals.

Figure 5:
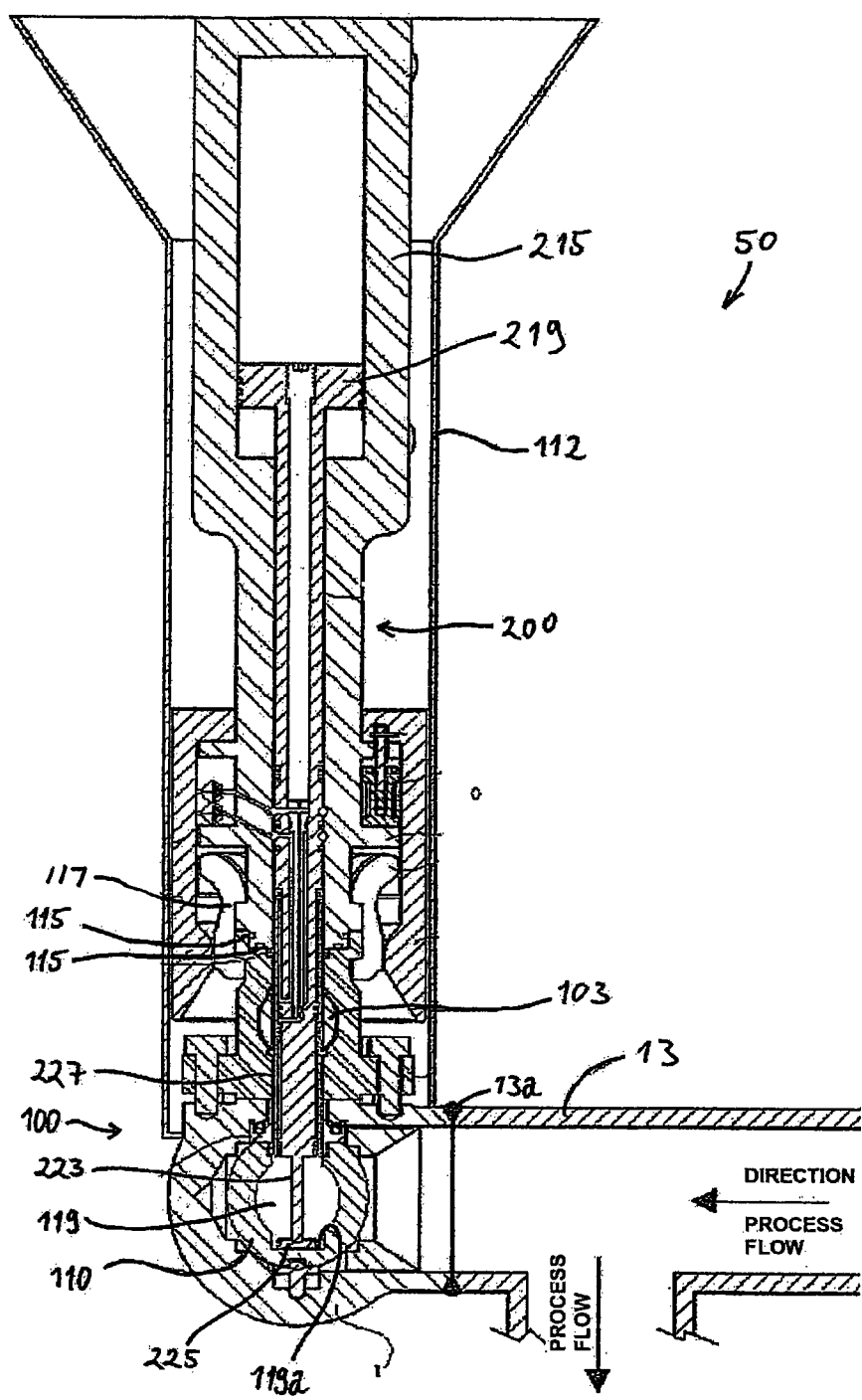
FIG. 5 shows a schematic cross section view of the assembly in FIG. 1, where an amount of fluid is confined in the receiving chamber.

The sampling organ 217 is moved through the bore 213 until the head 225 abuts against a recess 119*a* in the receiving chamber 119. Thereafter the chamber valve 110 is closed, as shown in FIG. 5, so that a representative amount of the fluid flow that flows through the pipe assembly 13 is confined in the receiving chamber 119.

Figure 6:
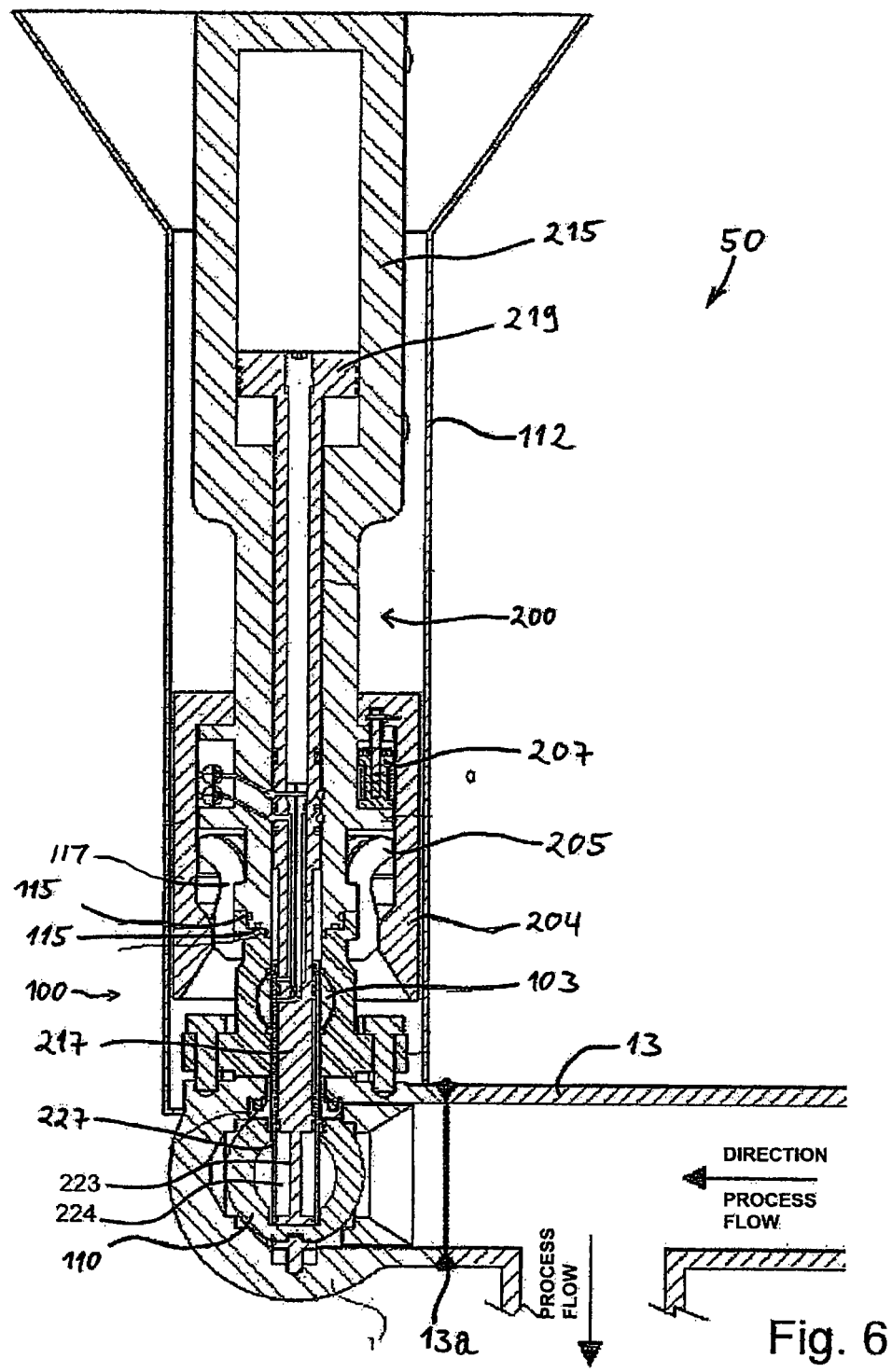
FIG. 6 shows a schematic cross section view of the assembly in FIG. 1, where a fluid sample is confined in a closed cavity.

As shown in FIG. 6, when the chamber valve 110 is closed towards the fluid flow, a sampling sleeve 227 is guided forwards to the head 225, so that the inner face of the sample sleeve 227 seals against the seals arranged peripherally on the head 225. The sampling sleeve 227 is actuated by hydraulics running through the hydraulic channels 229, 231, for upwardly and downwardly movement of the sampling sleeve 227, respectively. The channels 229, 231 are connected to controlled hydraulic sources 229*a*, 231*a*, schematically illustrated in FIG. 6. The sampling sleeve 227 comprises first and second piston heads 227*a*, 227*b*, for the hydraulic actuation of the sampling sleeve 227 in the bore 213 and on the outside of the sampling organ 217.

A sample of the fluid flow is now confined in a closable space 224 defined by the constricted diameter 223 of the sampling organ, the head 225 and the sampling sleeve 227. As will be understood by a person skilled in the art, this sample will not be representative of the composition of the flowing fluid, since the walls of the reception chamber 119 has oval walls. For instance, a column of oil between a water column and a gas column will have less vertical extension than it would if the reception chamber 119 had vertical walls, such as a cylinder. However, since the shape of the reception chamber 119 is known, one can easily calculate the correct composition of the fluid flow by means of the sealed off sample.

Furthermore, when the sampling sleeve 227 is moved into the reception chamber 119, until it seals against the seals in the head 225, some of the fluid in the reception chamber 119 will be displaced in order to give room for the volume represented by the sampling sleeve 227 in the reception chamber 119. This fluid will seep along a narrow slit between the sampling sleeve 227 and the bore 113 of the fixed part, and into the displacement space 233 which the sampling sleeve 227 leaves behind when it moves. The amount of fluid that seeps into the displacement space 233 will be known. Thus, although this fluid is lost from the reception chamber 119 and thus contributes to making the fluid sample non-representative, one will be able to calculate the composition in the fluid flow.

Preferably, in connection with the sampling organ 217 there is arranged various gauges for the characteristics of the fluid in the confined fluid sample. For instance, the sampling organ 217 can be provided with a pressure gauge (not shown), such as a PT 100 element. Furthermore, the sampling sleeve 227 and the part of the sampling organ having the constricted diameter 223 can be electrically connected as a capacitor. Thus the water fraction of the confined sample can be determinated in situ. There may also preferably be arranged a gauge for salinity, for instance in connection with the head 225, where the water fraction will gather due to gravity. It may involve a 3-pole salinity probe, as known by the person skilled in the art.

When the sampling sleeve 227 has confined the sample, as shown in FIG. 6, the chamber valve 110 is again opened towards the fluid flow and the sampling organ 217 is pulled back by means of the piston 219. The sampling sleeve 227 remains in place over the constricted diameter 223 and the head 225. When the sample is pulled into the bore 213 in the main body, the barrier valve 103 is also be closed. After pressure testing of the again closed chamber valve 110 and the barrier valve 103, the releasable part 200 can be disconnected from the fixed part 100 and be brought to the surface with the sample.

In addition to the embodiment described herein, one can also imagine an assembly of the sampling organ 217 with the constricted diameter 223 or another form of available sample space, the movable sampling sleeve 227, and possible measuring equipment (as indicated above), and the barrier valve 103 as such. Such an assembly could be used without the chamber valve 110, for instance directly on a flow pipe, preferably in connection with a constriction, bend or similar in the flow path.

When the releasable part 200 is removed, a dummy part (not shown) is preferably connected to the fixed part 100 in order to protect it. The dummy part can preferably seal against the seals 115 and thus constitute an additional barrier, as well as protecting the seals 115.

Figure 7:
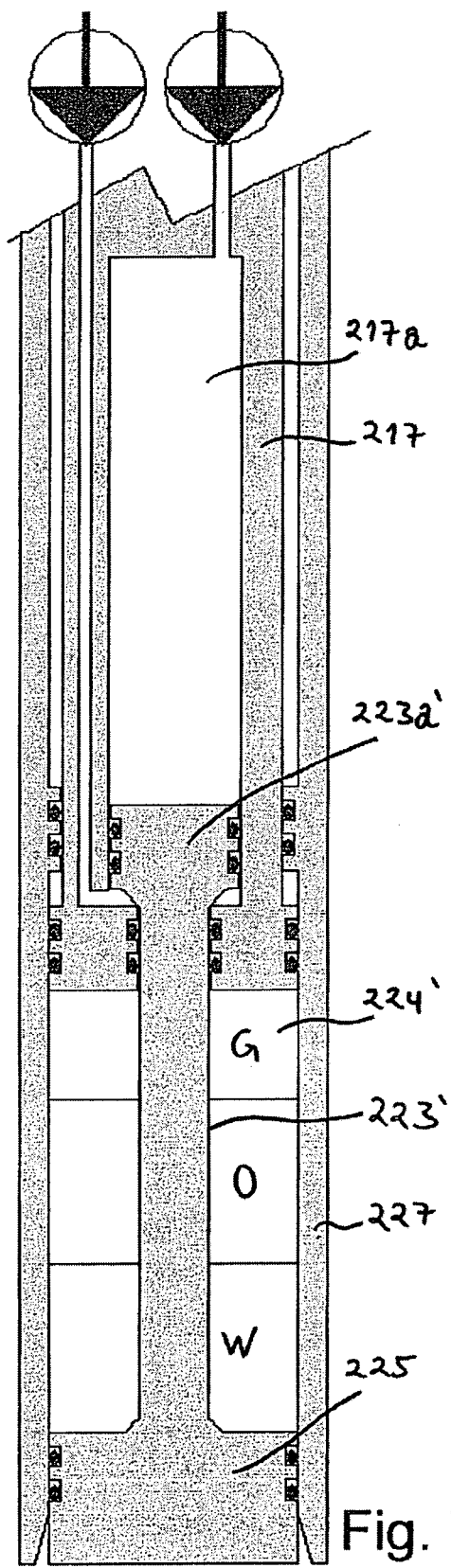
FIG. 7 shows a cross section of an embodiment of a sampling organ.
Figure 8:
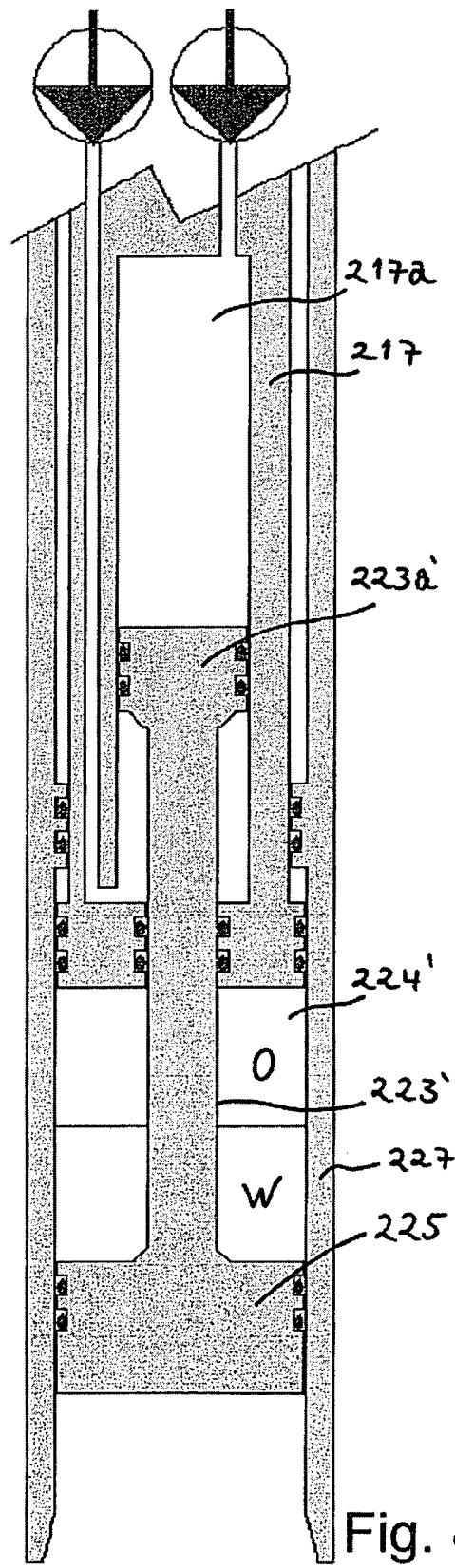
FIG. 8 shows the cross section of FIG. 7 in another position.

FIGS. 7 and 8 show a particular embodiment of the releasable part 200 of the assembly 50 according to the invention, for taking samples from a fluid flow. The figures show the end of the sampling organ 217, where the sampling sleeve 227 has been moved forward to the head 225 for confinement of a sample. In this embodiment the constricted part 223' is in the form of a piston rod that has a piston 223*a*' arranged in a piston chamber 217*a* in the sampling organ 217. On each side of the piston 223*a*' there is hydraulic pressure supply, schematically represented with two hydraulic pumps.

The situation in FIG. 7 shows a sample consisting of gas G, oil O and water W. With supply of hydraulic pressure below the piston 223*a*', the head 225 is led upwards so that the gas G in the sample is compressed into liquid phase and adsorbed in the liquid. This is shown in FIG. 8, where the sample now only comprises water W and oil O (or hydrocarbons in liquid form). By measuring the amount of hydraulic liquid that is used to compress the gas G, or the position of the head 225, one will know how much gas which has been compressed. This information can, along with the amount of water W and oil O, be used to calculate the composition of the fluid in the flow. An advantage of this solution is that one, during operation, can perform a test that shows the relation between gas and liquid, GVF (Gas-Volume-Fraction), and give feedback on this without having to take the sample to the surface. An additional advantage is that one may perform repetitive samples before disconnecting, and thus have a basis of calculation for the accuracy of GVF.

According to an aspect of the invention there is also provided a sampling organ as shown in FIG. 7 and FIG. 8 as such. That is, it can be provided such a sampling organ which can be used in connection with various assemblies, in addition to the assembly shown in FIG. 1 to FIG. 6. For instance, such an assembly can be used without removing a fluid sample from a pipe system. A sampling organ as shown in FIG. 7 and FIG. 8 can also advantageously be provided with gauges for fluid characteristics, such as gauges for salinity, pressure, capacitor, as mentioned above. Such an arrangement will be suited for repeated measurements in situ, so that an average of a plurality of measured results can be calculated for a plurality of different parameters. This without removing a fluid sample from the sampling place. As will be appreciated by a person skilled in the art, the arrangement shown in FIG. 7 and FIG. 8 will of course also be suited for bringing a fluid sample away from the sampling place, for instance to a laboratory.

The volume that is left by the head 225 during this movement can be vacuum.

FIG. 9 and FIG. 10 show a circular and rectangular shaped closing opening for the chamber valve 110, respectively. In order to provide a best possible representativity of the fluid that is confined in the receiving chamber 119, it is preferred that the closing opening is rectangular, as shown in FIG. 10.

In lieu of a ball valve, such as the chamber valve 110 shown in the example above, one may also imagine another type of valve that opens and closes for inflow to the receiving chamber 119. Thus, the receiving chamber 119 does not need to be arranged in a valve at all, but can on the other hand be a fixed closable chamber adapted to receive the sampling organ 217.

Furthermore, the fixed part 100 of the assembly 50 can be such that the releasable part 200 is mounted from below, contrary to the example described herein. It is advantageous to take the sample vertically, from above or from below, due to good representativity of the sample, while it due to operational reasons will be most advantageous to mount the releasable part from above. With particular adjustments one can even imagine that the releasable part 200 is mounted in a non-vertical position.

One can, furthermore, imagine that the assembly 50 according to the invention is mounted other places where there exist good representativity in the fluid flow, for instance after an obstruction in the process pipe. Such an obstruction can for instance be a constriction of the flow cross section, for instance a venturi form, or a body obstruction, for instance a ball or a cone, etc. In addition one may imagine performing the sampling in connection with a separator system, where one wants to control the effect of separation of fluids/particles or cleaning of water which is to be re-injected subsea. The advantage of such a system will be to contribute to quality assurance of separation and cleaning processes. This has both economical and environmental consequences, since an imperfect process will result in lost oil revenues and increased pollution of the cleaned process water.

In stead of sample sleeve 227 that is pushed axially over the constricted diameter 223 for confinement of a sample space, as described above, one may also imagine alternative embodiments for the sampling organ 217. For instance a rotating outer sleeve may be arranged, so that an opening in the outer sleeve is arranged over an opening in an outer wall of an inner sleeve, for inflow of fluid. After the inflow the two sleeves can be mutually rotated, so that the opening is closed.

Figure 11:
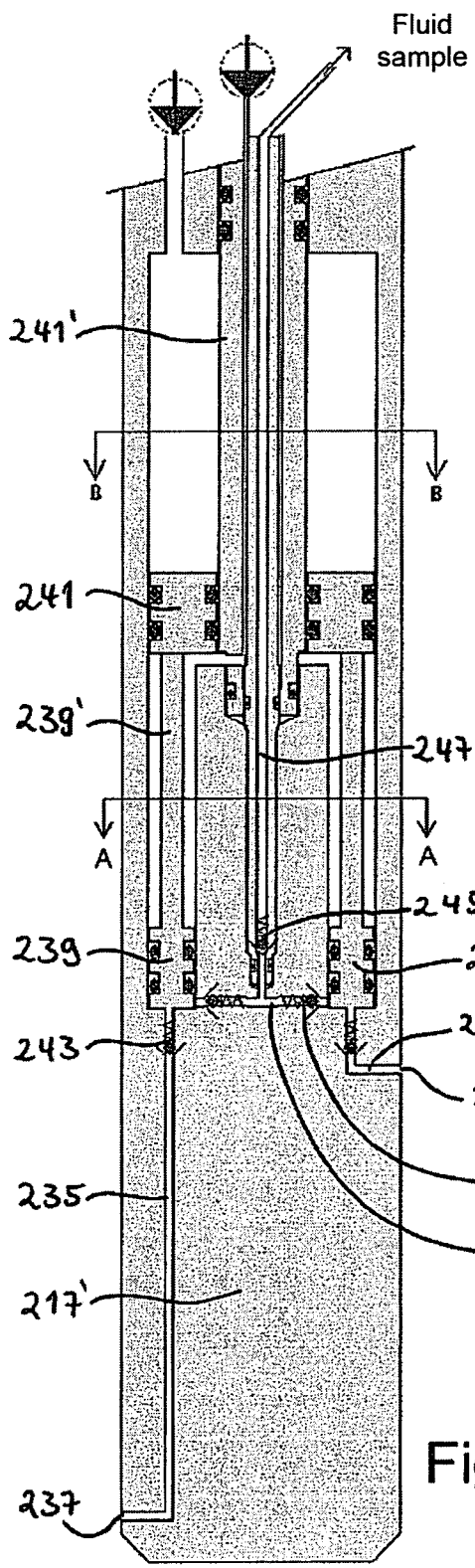
FIG. 11 shows a particular embodiment of a sampling organ.
Figure 12:
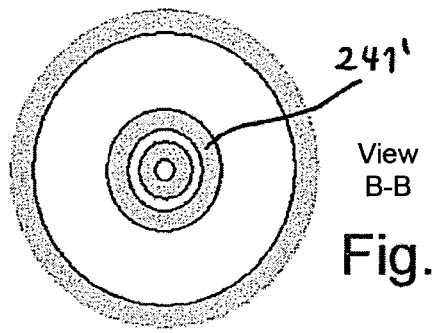
FIG. 12 shows a cross section through a sampling organ in FIG. 11.
Figure 13:
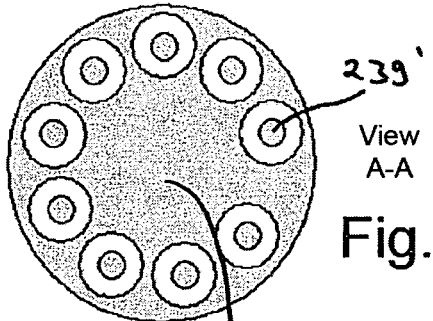
FIG. 13 shows another cross section through the sampling organ in FIG. 11.

An additional example of embodiment of a sampling organ 217' is shown in FIG. 11, FIG. 12, FIG. 13 and FIG. 14. FIG. 11 shows a cross section of an alternative sampling organ 217' adapted to be inserted into the receiving chamber 119, as described above. In its end part the sampling organ 217' has a plurality of sample channels 235 that extend parallel to the axis of the sampling organ 217'. Each sample channel 235 is connected to a mouth 237 in the side face of the sampling organ 217'. The mouths 237 are arranged at different axial positions in the sampling organ 217. When the sampling organ 217' is arranged in the receiving chamber 119 and a fluid sample is to be taken, a certain amount of fluid will be pulled in through each respective mouth 237 and sample channel 235. This step is provided by a common movement of a plurality of sample pistons 239. Each sample piston 239 is connected to a common piston 241 that is adapted to be hydraulically actuated in order to provide the common movement. FIG. 12 and FIG. 13 show cross sections through the sampling organ 217' through, respectively, the piston rod 241' of the common piston 241 and the piston rods 239' to which the sample pistons 239 are connected.

Figure 14:
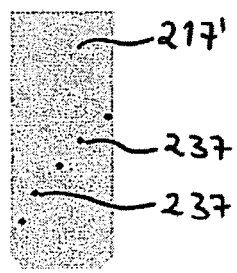
FIG. 14 shows a detailed view of an end part of the sampling organ in FIG. 11.

FIG. 14 shows, in a side view, schematically how the mouths 237 are distributed on the face of the sampling organ 217'. A sampling will thus result in a certain amount of fluid which is pulled from a plurality of different axial or vertical positions. In this example of embodiment the sampling organ 217' is provided with nine sample channels 235.

As appears from FIG. 11 each sample channel 235 is provided with a one-way valve 243 which results in that the fluid that is pulled in through the respective mouths 237 cannot flow back into the receiving chamber 119 (see FIG. 1). Furthermore, after one upwardly directed (with respect to the depiction in FIG. 11) movement of the sample pistons 239, an opposite downwardly movement of the sample pistons 239 will press the fluid sample through a common one-way valve 245 and a common sample channel 247. The fluid sample pulled out from the receiving chamber 119 will then be guided out from this part of the sampling organ 217. Preferably the fluid sample can be guided to a collecting chamber (not shown) arranged another place in the releasable part 200. In this way one may pull out a plurality of fluid samples, and in this way reduce possible measuring errors by repeating the process a plurality of times.

The technical elements in the embodiment of the sampling organ 217' shown in FIG. 11 that provide possibility of repetition, is only one of a plurality of possible embodiments. One may thus provide a sampling organ 217' adapted to pull in a fluid sample only once, as it does not comprise the common sample channel 247 with the one-way valve 245. It should also be underlined that the sampling organ 217' described herein with reference to FIG. 11 to FIG. 14 is not limited to use with an assembly as shown in FIG. 1 to FIG. 6, but can be used in connection with any kind of suitable sampling assembly, as will be understood by a person skilled in the art.

According to an aspect of the invention there is also provided an assembly which is simplified with respect to the embodiment shown in FIG. 1 to FIG. 6. Such an assembly comprises a ball valve or corresponding valve with a rotating inner valve body, where the valve body comprises a void. The inner body can thus be sphere shaped, but also for instance cylindrically shaped with a rotation axis parallel to the cylinder axis. The valve is connected to a flow path in such a manner that it with a first opening can let in fluid from a flowing fluid into the void, and then close this first opening by rotation of the inner body. Furthermore it is rotationally suspended about a rotational axis, wherein the void has an opening in the said rotational axis. In this manner fluid can be let out to an attached sample container by means of differential pressure. Alternatively a sampling device can be let into the inner void, corresponding to the embodiment shown in FIG. 1 to FIG. 6, as described above. One can also imagine that measuring equipment is inserted into the void when the valve has closed the opening towards the fluid flow, in order to perform measurements without removing a fluid sample from the void.

A person skilled in the art will appreciate that the separate technical elements described herein can be combined in various ways and also be used alone or in connection with assemblies that are not described herein.

The invention claimed is:

1. A sampling arrangement adapted for extracting a fluid sample from a fluid flowing in a flow path, the sampling arrangement comprising:
a sampling valve comprising an outer body and an in this suspended inner rotating body, where the inner rotating body is rotationally suspended about a rotation axis and comprises a cavity with a first opening adapted to be rotated into and out of fluid connection with the flowing fluid, and a second opening that faces in a direction parallel with the rotation axis of the inner rotating body, wherein the first opening and the second opening define a singular path through the inner rotating body and wherein the second opening receives a sampling organ moving in a direction parallel to the rotation axis.

2. The sampling arrangement according to claim 1, wherein the sampling valve comprises a ball valve.

3. An assembly adapted to provide a sample from a flowing fluid that flows in a flow path, wherein the assembly comprises:
a releasable part; and
a fixed part that is adapted for releasable connection to the releasable part, wherein the fixed part comprises:
a receiving chamber that is provided with a closable fluid opening for fluid communication to the flowing fluid;
a closable receiving opening for reception of a sampling organ into the receiving chamber along a direction perpendicular to a facing direction of the closable receiving opening; and
wherein the releasable part comprises
said sampling organ, which is adapted to be moved into the receiving chamber when the releasable part is connected to the fixed part.

4. The assembly according to claim 3, wherein the receiving chamber is arranged in a ball of a ball valve, where the ball has a cavity with an opening that constitutes said closable fluid opening, as well as an opening for reception of the sampling organ.

5. The assembly according to claim 4, wherein the ball is rotatable about a rotation axis and the rotation axis is parallel to the opening for reception of the sampling organ and/or extends through this opening.

6. The assembly according to claim 3, wherein the fixed part is connected to the flow path in association with a flow obstacle that provides mixing of components of the flowing fluid in a section of the receiving chamber.

7. The assembly according to claim 6, wherein the flow obstacle is a change of direction of a flow direction, and that the fixed part is connected to a blind end of a T-shaped part of the flow path.

8. The assembly according to claim 6, wherein the flow obstacle is in form of a constriction of a flow cross section.

9. The assembly according to claim 3, wherein:
the sampling organ is bar shaped and has a section with constricted cross section that forms a closable cavity; and
the releasable part further comprises a sample sleeve that is arranged to be pushed over the section with constricted cross section, to seal against a head in one end of the section having constricted cross section.

10. The assembly according to claim 3, wherein the sampling organ is provided with a plurality of mouths and associated sample channels adapted to pull in a volume of the flowing fluid in the receiving chamber, wherein at least some of the mouths are arranged in different axial position on the sampling organ.

11. The assembly according to claim 10, wherein the sampling organ further comprises a common sample channel for guiding of a fluid sample pulled in through the mouths, thereby setting the sampling organ in condition to pull in another fluid sample from the receiving chamber.

12. The assembly according to claim 3, wherein the fixed part comprises a barrier valve adapted to close the closable receiving opening.

13. An assembly adapted to provide a sample from a flowing fluid that flows in a flow path, wherein assembly comprises:
a releasable part; and
a fixed part that is adapted for releasable connection to the releasable part, wherein the fixed part comprises:
a receiving chamber that is provided with a closable fluid opening for fluid communication to the flowing fluid;
a closable receiving opening for reception of a sampling organ into the receiving chamber along a direction perpendicular to a facing direction of the closable fluid opening; and
wherein the releasable part comprises
said sampling organ, which is adapted to be moved into the receiving chamber when the releasable part is connected to the fixed part;
wherein the sampling organ is bar shaped and has a section with constricted cross section that forms a closable cavity; and
wherein the releasable part further comprises a sample sleeve that is arranged to be pushed over the section with constricted cross section, to seal against a head in one end of the section having constricted cross section.

14. An assembly adapted to provide a sample from a flowing fluid that flows in a flow path, wherein assembly comprises:
a releasable part; and
a fixed part that is adapted for releasable connection to the releasable part, wherein the fixed part comprises:
a receiving chamber that is provided with a closable fluid opening for fluid communication to the flowing fluid;
a closable receiving opening for reception of a sampling organ into the receiving chamber along a direction perpendicular to a facing direction of the closable fluid opening;
wherein the releasable part comprises
said sampling organ, which is adapted to be moved into the receiving chamber when the releasable part is connected to the fixed part; and wherein the sampling organ is provided with a plurality of mouths and associated sample channels adapted to pull in a volume of the flowing fluid in the receiving chamber, wherein at least some of the mouths are arranged in different axial position on the sampling organ.

* * * * *